United States Patent [19]
Hwang et al.

[11] Patent Number: 5,905,089
[45] Date of Patent: May 18, 1999

[54] USE OF SESQUITERPENE LACTONES FOR TREATMENT OF SEVERE INFLAMMATORY DISORDERS

[75] Inventors: Daniel H. Hwang; Nikolaus H. Fischer, both of Baton Rouge, La.

[73] Assignee: Board of Supervisors of Louisiana State University and Agricultural and Mechanical College, Baton Rouge, La.

[21] Appl. No.: 09/059,480

[22] Filed: Apr. 13, 1998

Related U.S. Application Data

[60] Provisional application No. 60/080,224, Apr. 14, 1997.

[51] Int. Cl.$^6$ ..................................................... A61K 31/34
[52] U.S. Cl. ............................................................. 514/468
[58] Field of Search ............................................. 514/468

[56] References Cited

U.S. PATENT DOCUMENTS

| 4,758,433 | 7/1988 | Johnson et al. | 424/195.1 |
| 5,384,121 | 1/1995 | Rhodes | 424/195.1 |

OTHER PUBLICATIONS

U.S. application No. 08/394,148, Feng et al., filed Feb. 24, 1995.

I. Hall et al., "Anti–Inflammatory Activity of Sesquiterpene Lactones and Related Compounds," *J. Pharm. Sci.*, vol. 68, pp. 537–542 (1979).

I. Hall et al., "Mode of Action of Sesquiterpene Lactones as Anti–Inflammatory Agents," *J. Pharm. Sci.*, vol. 69, pp. 537–543 (1980).

K. Lee, "Antitumor Agents. 32. Synthesis and Antitumor Activity of Cyclopentenone Derivatives Related to Helenalin," *J. Med. Chem.*, vol. 21, pp. 819–822 (1978).

K. Lee et al., "Cytotoxicity of Sesquiterpene Lactones," *Cancer Research*, vol. 31, pp. 1649–1654 (1971).

J. Cassady, "Potential Antitumor Agents. Synthesis, Reactivity, and Cytotoxicity of α–Methylene Carbonyl Compounds," *J. Med. Chem.*, vol. 21, pp. 815–819 (1978).

G. Howie et al., "Potential Antitumor Agents. Synthesis of Bifunctional α–Methylene–γ–butyrolactones," *J. Med. Chem.*, vol. 19, pp. 309–313 (1976).

S. Kupchan, "Tumor Inhibitors. 69. Structure–Cytotoxicity Relationships among the Sesquiterpene Lactones," *J. Med. Chem.*, vol. 14, pp. 1147–1152 (1971).

T. Waddell et al., "Antitumor Agents: Structure–Activity Relationships in Tenulin Series," *J. Pharm. Sci.*, vol. 68, pp. 715–718 (1979).

R. Stone, "Search for Sepsis Drugs Goes On Despite Past Failures," *Science*, vol. 264, pp. 365–367 (1994).

A. Fein, "Treatment of Severe Systemic Inflammatory Response Syndrome and Sepsis with a Novel Bradykinin Antagonist, Deltibant (CP–0127)," *J. Am. Med. Assoc.*, vol. 277, pp. 482–487 (1997).

P. Chanmugam, "Radicicol, a Protein Tyrosine Kinase Inhibitor, Suppresses the Expression of Mitogen–Inducible Cyclooxygenase in Macrophages Stimulated with Lipopolysaccharide and in Experimental Glomerulonephritis," *J. Biol. Chem.*, vol. 270, pp. 5418–5426 (1995).

A. Novogrodsky et al., "Prevention of Lipopolysaccharide–Induced Lethal Toxicity by Tyrosine Kinase Inhibitors," *Science*, vol. 264, pp. 1319–1322 (1994).

T. Akiyama et al., "Genistein, a Specific Inhibitor of Tyrosine–Specific Protein Kinases," *Journal of Biological Chemistry*, vol. 262, pp. 5592–5595 (1986).

Hwang et al., "Inhibition of the Expression of Inducible Cyclooxygenase and Proinflammatory Cytokines by Sesquiterpene Lactones in Macrophages Correlates with the Inhibition of MAP Kinases," *Biochem. and Biophys. Res. Comm.*, vol. 226, pp. 810–818 (1996).

*Primary Examiner*—Keith D. MacMillan
*Attorney, Agent, or Firm*—Bonnie J. Davis; John H. Runnels

[57] ABSTRACT

Sesquiterpene lactones are useful in suppressing the early proinflammatory cytokines, and in ameliorating septic shock and other severe inflammatory disorders. Sesquiterpene lactones with an α-methylene-γ-lactone functional group suppress the expression of the inducible cyclooxygenase-2 and proinflammatory cytokines (Interleukin-1α and β, IL-1, and tumor necrosis factor-α (TNFα)) in mammalian macrophages stimulated with lipopolysaccharide. This suppression correlated with the inhibition of protein-tyrosine phosphorylation including the mitogen-activated protein kinases.

24 Claims, 6 Drawing Sheets

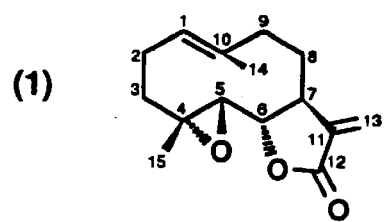
(1)
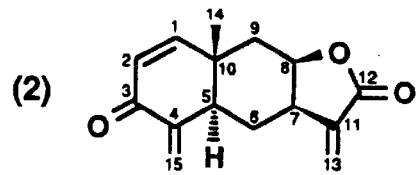
(2)
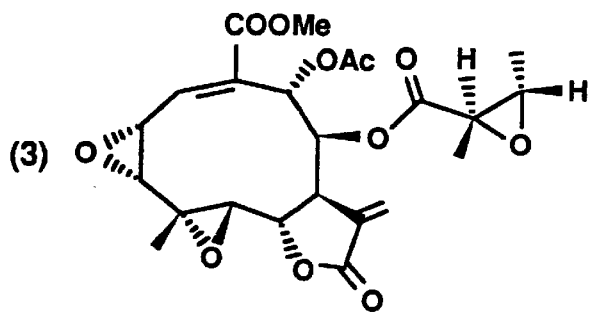
(3)
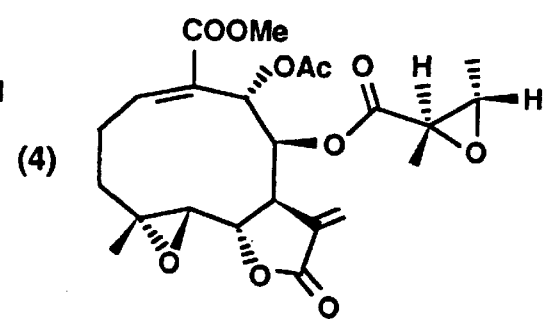
(4)
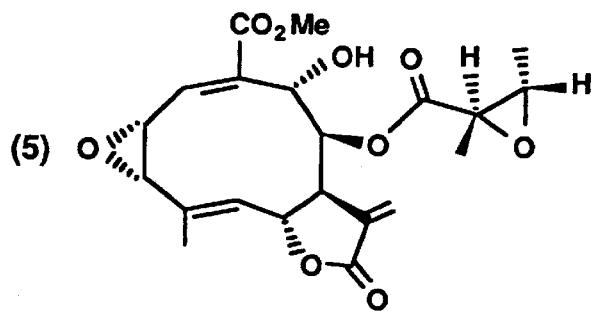
(5)
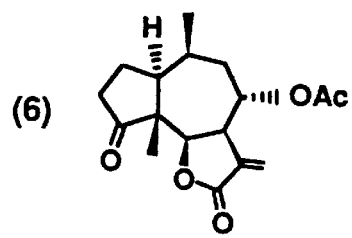
(6)
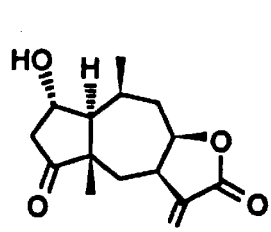
(7)
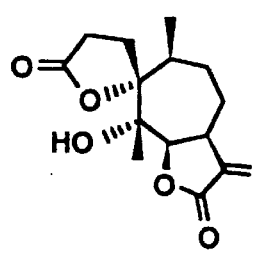
(8)
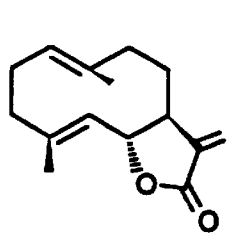
(9)
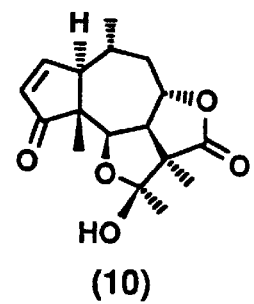
(10)
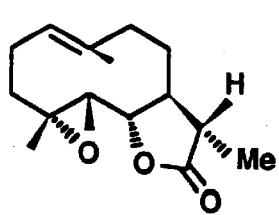
(11)
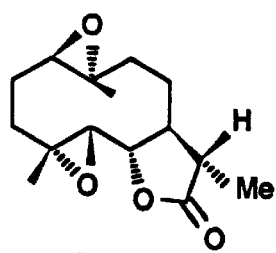
(12)
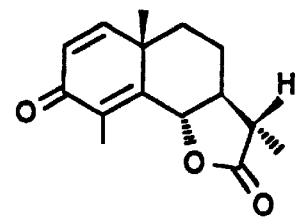
(13)
FIGURE 1

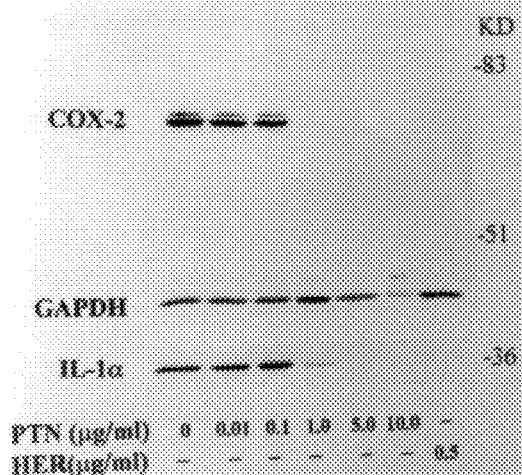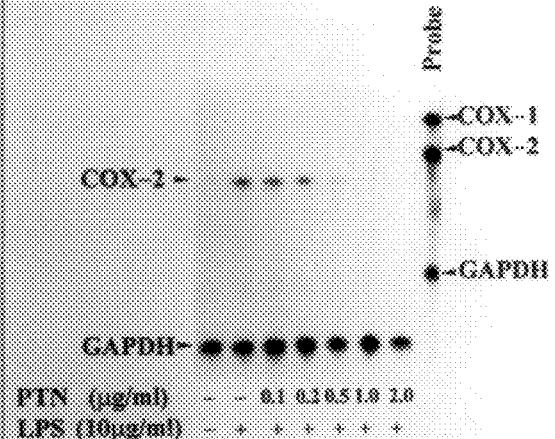

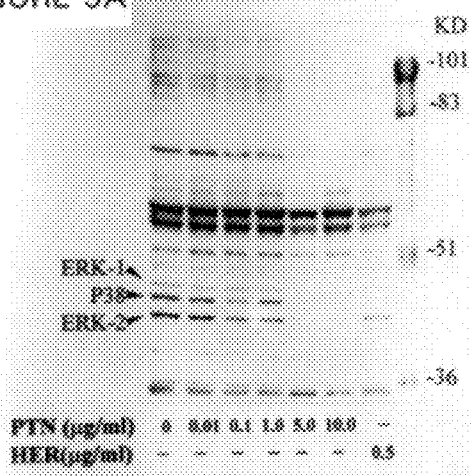
FIGURE 5A
FIGURE 5B
FIGURE 5C
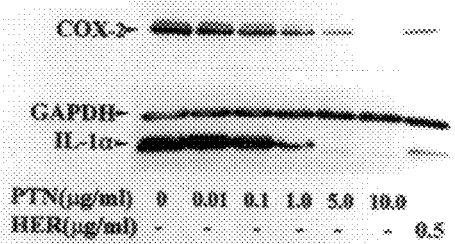
FIGURE 5D

USE OF SESQUITERPENE LACTONES FOR TREATMENT OF SEVERE INFLAMMATORY DISORDERS

The benefit of the Apr. 14, 1997 filing date of provisional application 60/080,224 (which was a conversion of nonprovisional application 08/839,514), now abandoned, is claimed under 35 U.S.C. § 119(e).

The development of this invention was partially funded by the Government under grant R01 DK-41868 from the National Institute of Health and grant 93-37200-8961 from the U.S. Department of Agriculture. The Government may have certain rights in this invention.

This invention pertains to sesquiterpene lactones and sesquiterpene lactone-containing plant extracts and preparations for pharmaceutical uses, particularly the use of sesquiterpene lactones for the treatment of severe inflammatory disorders, for example, sepsis, septic shock, or septicemia.

A large number of sesquiterpene lactones and their sources are described in N. Fischer et al., "The Biogenesis and Chemistry of Sesquiterpene Lactones," in W. Herz et al. (eds.), *Prog. Chem. Org. Nat. Prod.* Springer-Verlag, vol. 38, pp 47–390 (1979), the complete disclosure of which is incorporated by reference.

Sesquiterpene lactones, especially those containing an α-methylene-γ-lactone group, have been shown to possess activity against tumor growth and general inflammation. I. Hall et al., "Anti-Inflammatory Activity of Sesquiterpene Lactones and Related Compounds," *J. Pharm. Sci.,* vol. 68, pp. 537–542 (1979) discloses that sesquiterpene lactones possess activity against general inflammatory reactions. See also I. Hall et al., "Mode of Action of Sesquiterpene Lactones as Anti-Inflammatory Agents," *J. Pharm. Sci.,* vol. 69, pp. 537–543 (1980).

K. Lee, "Antitumor Agents. 32. Synthesis and Antitumor Activity of Cyclopentenone Derivatives Related to Helenalin," *J. Med. Chem.,* vol. 21, pp. 819–822 (1978) discloses that the sesquiterpene lactone helenalin and certain related compounds had some antitumor activity. See also K. Lee et al., "Cytotoxicity of Sesquiterpene Lactones," *Cancer Research,* vol. 31, pp. 1649–1654 (1971).

J. Cassady, "Potential Antitumor Agents. Synthesis, Reactivity, and Cytotoxicity of α-Methylene Carbonyl Compounds," *J. Med. Chem.,* vol. 21, pp. 815–819 (1978) reports antitumor activity of certain sesquiterpene lactones and related compounds. See also G. Howie et al., "Potential Antitumor Agents. Synthesis of Bifunctional α-Methylene-γ-butyrolactones," *J. Med. Chem.,* vol. 19, pp. 309–313 (1976).

S. Kupchan, "Tumor Inhibitors. 69. Structure-Cytotoxicity Relationships among the Sesquiterpene Lactones," *J. Med. Chem.,* vol. 14, pp. 1147–1152 (1971) discloses the structures of several cytotoxic sesquiterpene lactones, reports that an α-methylene-γ-lactone group was found to be essential for significant cytotoxic activity, and discloses other features associated with increased activity among those compounds.

T. Waddell et al., "Antitumor Agents: Structure-Activity Relationships in Tenulin Series," *J. Pharm. Sci.,* vol. 68, pp. 715–718 (1979) discloses antitumor activity of the sesquiterpene lactone tenulin and related compounds.

There are no prior reports of using a sesquiterpene lactone to treat severe inflammatory disorders such as sepsis, septic shock, or septicemia.

Septic shock and multiple-organ failure are catastrophic consequences of an invasive infection. Septic shock has been estimated to occur in more than 500,000 cases per year in the United States alone. Septic shock is the most common cause of death in non-coronary, intensive care units. As more antibiotic-resistant strains of bacteria evolve, the incidence of septic shock is expected to increase. Overall mortality rates from septic shock range from 30% to 90%. Aggressive antibiotic treatment and timely surgical intervention are the main therapies, but in many cases are insufficient. The search for new drug therapies has not been successful. R. Stone, "Search for Sepsis Drugs Goes On Despite Past Failures," *Science,* vol. 264, pp. 365–367 (1994). See, e.g., A. Fein, "Treatment of Severe Systemic Inflammatory Response Syndrome and Sepsis with a Novel Bradykinin Antagonist, Deltibant (CP-0127)," *J. Am. Med. Assoc.,* vol. 277, pp. 482–487 (1997), reporting small, but not statistically significant, improvements in 28-day mortality compared to placebo when the compound deltibant was administered to human patients suffering systemic inflammatory response syndrome and presumed sepsis. (Deltibant is a dimer of two peptides joined to one another by a linker.)

Lipopolysaccharide (LPS) is believed to be the principal agent responsible for inducing sepsis syndrome, which includes septic shock, systemic inflammatory response syndrome, and multiorgan failure. Sepsis is a morbid condition induced by a toxin, the introduction or accumulation of which is most commonly caused by infection or trauma. The initial symptoms of sepsis typically include chills, profuse sweating, irregularly remittent fever, prostration and the like; followed by persistent fever, hypotension leading to shock, neutropenia, leukopenia, disseminated intravascular coagulation, acute respiratory distress syndrome, and multiple organ failure.

LPS, also known as endotoxin, is a toxic component of the outer membrane of Gram-negative microorganisms (e.g., *Escherichia coli, Klebsiella pneumonia, Pseudomonas aeruginosa*). Compelling evidence supports the toxic role of LPS; all pathophysiological effects noted in humans during Gram-negative sepsis can be duplicated in laboratory animals by injection of purified LPS. The mechanism by which LPS activates responsive cells is complex and not fully understood. The host response to Gram-negative bacterial infection depends on effector cell recognition of the bacteria, LPS, or both, and involves both serum proteins and cell membrane receptors. When bacteria and LPS are removed via endocytosis and phagocytosis by reticuloendothial cells, concomitant activation of the host immune response by LPS results in the secretion of cytokines by activated macrophages, which in turn can trigger the exaggerated host responses associated with septic shock.

The normal immune response begins when neutrophils squeeze through the blood-vessel walls searching for bacterial pathogens in the surrounding tissue. Neutrophils can kill bacteria directly by releasing toxic chemicals or enzymes, such as elastase or collagenase. The neutrophils also attract other leukocytes to the area, including lymphocytes, macrophages, and monocytes, the last two of which release powerful immune-response activators called cytokines. The cytokines, in turn, stimulate more immune cell activity and increase the number of cells coming to the area by making the blood-vessel wall more permeable. Then, as the number of bacteria decreases, other cytokines signal to bring the normal immune response to an end.

If the cutoff mechanism fails, however, sepsis can begin. In sepsis, humoral and cellular mediators cascade in a process that becomes at least temporarily independent of the underlying infection. Excess neutrophils and macrophages are drawn to the site of infection, releasing excess immune-stimulating cytokines, eventually triggering the release of substances that damage the blood-vessel wall. More monocytes and macrophages come to the site and release more cytokines. Eventually, the blood vessels are so damaged and leaky that blood pressure falls and the blood can no longer supply nutrients to the body's organs. Entire organs can begin to shut down. Many patients die after losing the function of two or more organs.

Two cytokines that play an important role in sepsis are interleukin-1 (IL-1) and tumor necrosis factor-alpha (TNFα). These two polypeptides can raise body temperature, increase the expression of adhesion molecules on neutrophils and endothelial cells (promoting adhesion of leukocytes), stimulate the production of vasodilating prostaglandins (thus increasing the permeability of blood vessels), trigger the release of other cytokines, stimulate neutrophils, and activate fibroblasts. All these processes enhance the probability of organ failure seen in severe septicemia. Drug therapies that targets only one of these two cytokines have proved ineffective. See Stone (1994). Drug therapies that are effective against general inflammatory responses have not proven to be effective against the cascading acute inflammation that produces septicemia. There is a need for drugs that can inhibit this cascading system at the beginning steps of production of IL-1 and TNFα.

Other important cytokines, chemokines, and other proteins having proinflammatory activity include interferon-gamma (IFN-γ), interleukin-6 (IL-6), macrophage chemotactic protein (MCP), inducible nitric oxide synthetase (iNOS), mitogen-activated protein kinases (MAPKs), macrophage inflammatory protein, KC/CINC (growth related gene), tissue factor (TF), granulocyte-macrophage-colony stimulating factor (GM-CSF) and phosphotyrosine phosphatase (PTPase).

Prostaglandins are also involved in the proinflammatory response; e.g., prostaglandins increase the permeability of the blood-vessel wall. Cyclooxygenase (COX; prostaglandin endoperoxide synthase) catalyzes the conversion of arachidonic acid to prostaglandin (PG) endoperoxide (PGH2), which is the rate limiting step in prostaglandin biosynthesis. Two isoforms of COX have been cloned from animal cells: the constitutively expressed COX-1, and the mitogen-inducible COX-2. Prostaglandins produced as a result of the activation of COX-1 may have physiological functions such as the antithrombogenic action of prostacyclin released by the vascular endothelium, and the cytoprotective effect of PGs produced by the gastric mucosa. However, COX-2 is the enzyme expressed following the activation of cells by various proinflammatory agents including cytokines, endotoxin and other mitogens. These observations suggest that COX-2 instead of COX-1 may be responsible for inducing production of the prostaglandins involved in inflammation. Only a few pharmacological agents that suppress the expression of COX-2 without affecting COX-1 have not been identified, for example, glucocorticoids and radicicol.

There is a need for compounds that selectively inhibit COX-2, and that act as potent anti-inflammatory agents, with minimal side effects. To prevent septicemia, such a compound should also inhibit the production of a wide variety of proinflammatory cytokines, especially TNFα and IL-1, chemokines, and protein-tyrosine kinases.

Protein-tyrosine kinases (PTK) play a key role in initiating both receptor-mediated and non-receptor-mediated signal transduction pathways in eukaryotic cells. Increased PTK activity has been associated with cancers and with acute inflammatory responses such as septic shock.

Lipopolysaccharide (LPS) antigen activates macrophages, monocytes, and neutrophils, and the activated cells produce proinflammatory cytokines and lipid mediators that initiate and amplify inflammatory responses. LPS also stimulates protein tyrosine phosphorylation of mitogen-activated protein kinases (MAPKs) in macrophages. Suppression of the LPS-induced tyrosine phosphorylation results in inhibition of the expression of proinflammatory cytokines and of COX-2. We have shown that the activation of MAPKs is required for the expression of COX-2 (our laboratory, unpublished data).

P. Chanmugam, "Radicicol, a Protein Tyrosine Kinase Inhibitor, Suppresses the Expression of Mitogen-Inducible Cyclooxygenase in Macrophages Stimulated with Lipopolysaccharide and in Experimental Glomerulonephritis," *J. Biol. Chem.*, vol. 270, pp. 5418–5426 (1995) discloses that radicicol, a protein-tyrosine kinase inhibitor, suppresses the expression of mitogen-inducible cyclooxygenase 2 in macrophages stimulated with lipopolysaccharide. See also co-pending patent application Ser. No. 08/394,148, filed Feb. 24, 1995, which is assigned in part to the assignee of the present application.

Inhibitors of protein-tyrosine kinases have been shown to be effective in decreasing mortality in LPS-induced septicemia. A. Novogrodsky et al., "Prevention of Lipopolysaccharide-Induced Lethal Toxicity by Tyrosine Kinase Inhibitors," *Science*, vol. 264, pp. 1319–1322 (1994) discloses that protein tyrosine kinase inhibitors of the tyrphostin AG126 family protected mice against lipopolysaccharide-induced lethal toxicity.

Thus lipopolysaccharide (LPS) stimulates protein tyrosine phosphorylation in macrophages and induces the expression of the mitogen-inducible cyclooxygenase COX-2 and TNFα. PTK inhibitors suppress the expression of cyclooxygenase and TNFα in macrophages. The synthetic PTK inhibitors, tyrphostins, have been shown to prevent LPS-induced lethal toxicity in mice. These results indicate that PTK inhibitors may be effective therapeutic agents for septic shock and other acute inflammatory disorders.

The PTK inhibitors reported have been derived from the class of natural products called flavonoids, e.g., quercetin, genistein, levendustin A, erbstatin and herbimycin A. T. Akiyama et al., "Genistein, a Specific Inhibitor of Tyrosine-Specific Protein Kinases," *Journal of Biological Chemistry*, vol. 262, pp. 5592–5595 (1986) discloses that genistein, an isoflavone, inhibited the tyrosine-specific protein kinase activity of the epidermal growth factor receptor in vitro. Synthetic PTK inhibitors include tyrphostins, which contain the benzylidene moiety of erbstatin and other arylidene compounds, and a specific inhibitor of the epidermal growth factor receptor tyrosine kinase. There is no prior report of a sesquiterpene lactone inhibiting a protein-tyrosine kinase.

U.S. Pat. No. 4,758,433 discloses that sesquiterpene lactones derived from *Tanacetum parthenium* are useful in treating migraine, and that they may also be useful in treating asthma and arthritis.

U.S. Pat. No. 5,384,121 discloses a method for extracting sesquiterpene lactones from *Tanacetum parthenium*.

We have discovered that sesquiterpene lactones possessing an α-methylene γ-lactone group suppress the expression of the inducible cyclooxygenase-2, and also suppress the proinflammatory cytokines interleukin-1α, interleukin-1β, IL-1, and tumor necrosis factor-α(TNFα), and chemokines in mammalian macrophages stimulated with lipopolysaccharide. These sesquiterpene lactones also inhibit protein-tyrosine phosphorylation, including the mitogen-activated protein kinases. Sesquiterpene lactones are useful in suppressing early proinflammatory cytokines and proteins, and in ameliorating severe inflammatory disorders, including sepsis, septic shock, and septicemia.

BRIEF DESCRIPTION OF THE DRAWINGS

FIG. 1 illustrates the chemical structures of representative sesquiterpene lactones.

FIG. 3A illustrates the dose-dependent inhibition of the expression of COX-2 and IL-1α proteins by parthenolide.

FIG. 3B illustrates the dose-dependent inhibition of the steady state levels of COX-2 and GAPDH mRNAs by parthenolide.

FIG. 5A illustrates the dose-dependent inhibition of protein tyrosine phosphorylation and kinase activity of extracellular signal-regulated protein kinase-1 (ERK-1) and -2 (ERK-2) by parthenolide and herbimycin A as measured by antiphosphotyrosine immunoblot.

FIG. 5B illustrates the dose-dependent inhibition of protein tyrosine phosphorylation and kinase activity of ERK-1 and ERK-2 by parthenolide and herbimycin A as measured by c-Jun N-terminal kinase-1 (JNK-1) immunoblot.

FIG. 5C illustrates the dose-dependent inhibition of protein tyrosine phosphorylation and kinase activity of ERK-1 and ERK-2 as measured by an in-gel kinase assay using myelin basic protein (MBP) as a substrate.

FIG. 5D illustrates the dose-dependent inhibition of protein tyrosine phosphorylation and kinase activity of ERK-1 and ERK-2 as measured by COX-2, IL-1α, and GAPDH immunoblots.

Figure 2:
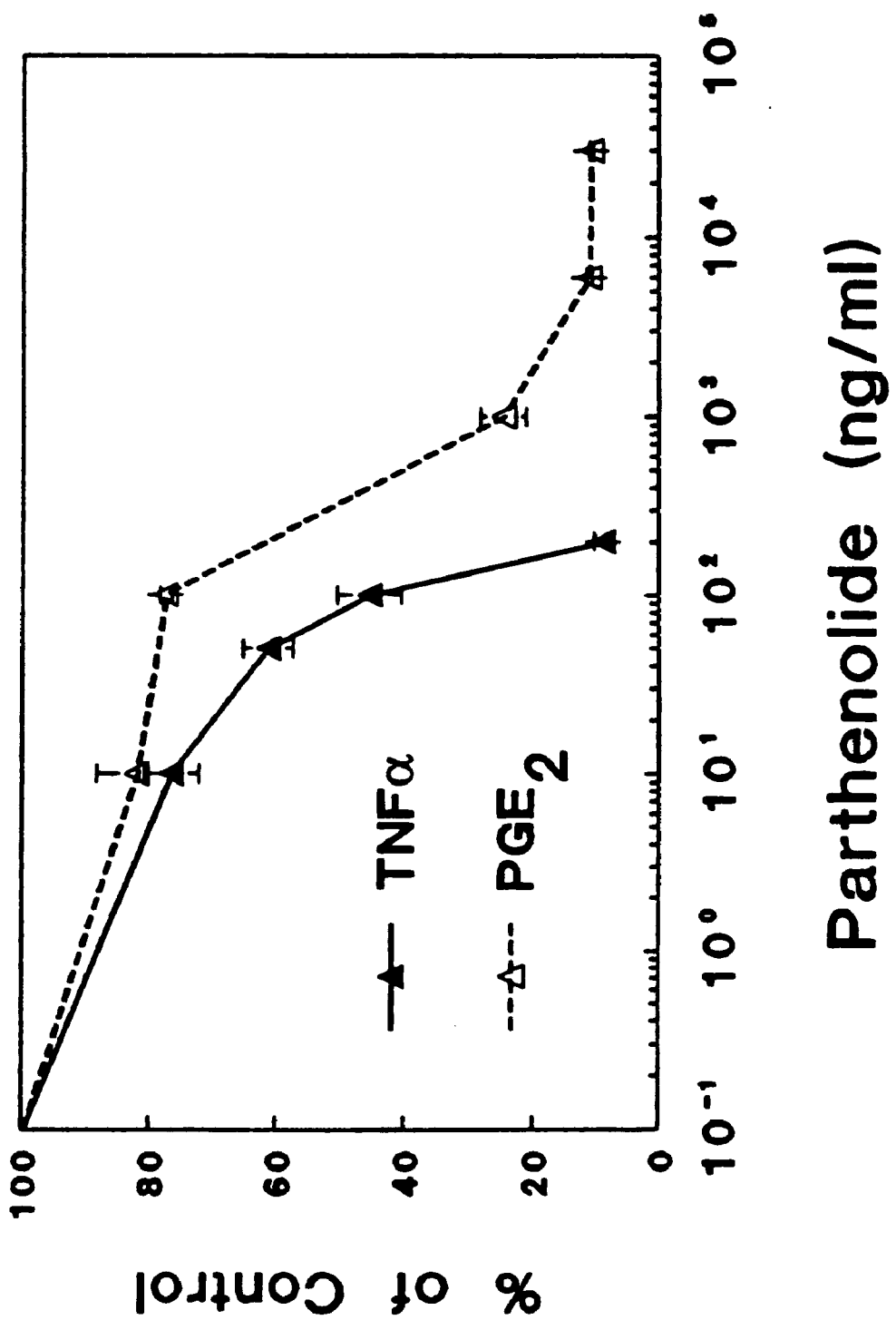
FIG. 2 illustrates observed dose-response for parthenolide inhibition of de novo synthesis of COX-2 and TNFα in LPS-stimulated macrophages.

The present invention provides a new use for the class of compounds known as sesquiterpene lactones, especially the subclass containing an α-methylene-γ-lactone moiety. Representative sesquiterpene lactones have been observed to inhibit IL-1, TNFα, and protein tyrosine kinases.

In a preferred embodiment, the present invention provides a method of treating a severe inflammatory disorder in a mammal, including a human, comprising administering to the mammal with the disorder a therapeutically effective amount of a sesquiterpene lactone having an α-methylene-γ-lactone group.

Sesquiterpenes are terpene compounds with fifteen carbon atoms; the biogenesis of a naturally-occurring sesquiterpenes is derivation from three mevalonic acid molecules as starting materials. Sesquiterpene lactones are a subclass of sesquiterpenes having a lactone functionality; a lactone is a cyclic ester. Many sesquiterpene lactones contain an exocyclic methylene lactone group, the α-methylene-γ-lactone moiety. See N. Fischer et al. (1979). Sesquiterpene lactones with the α-methylene-γ-lactone moiety show increased bioactivity if at least one of the following additional alkylating functional groups is present: an epoxide, a cyclopentenone, a cyclohexenone, a cyclohexadienone, an α,β-unsaturated ester, an α,β-epoxy ester, an α,β-unsaturated aldehyde, or an α, β-unsaturated ketone.

FIG. 1 illustrates the structures of representative sesquiterpene lactones. Compounds (1)–(10) contain an α-methylene-γ-lactone moiety. Compound (1), parthenolide, contains an epoxide moiety. Compound (2), encelin, contains a cyclohexadienone moiety. Compounds (3)–(5), leucanthin B, enhydrin, and melampodin, respectively, contain an α,β-unsaturated ester and α,β-expoxy ester side chains. Compounds (6)–(9) contain only the α-methylene-γ-lactone moiety. Compound (10) contains a cyclopentenone group. Compounds (11)–(12), 11,13-dihydroparthenolide and 1,10-epoxy-11,13-dihydroparthenolide, respectively, are derivatives of parthenolide that have lost the α-methylene-γ-lactone moiety. Compound (13), santonin, contains the epoxide moiety, but does not contain the α-methylene-γ-lactone moiety. Only the first ten compounds were found to be active.

As used herein, the term "active sesquiterpene lactone" refers to a sesquiterpene lactone that has an α-methylene-γ-lactone functional group, and that is capable of inhibiting or reducing the severity of a severe inflammatory response. Such active sesquiterpene lactones may be used in various combinations or mixtures.

An active sesquiterpene lactone may be administered to a patient by any suitable means, including parenteral, subcutaneous, intrapulmonary, and intranasal administration. Parenteral infusions include intramuscular, intravenous, intraarterial, or intraperitoneal administration. Active sesquiterpene lactone may also be administered transdermally, for example in the form of a slow-release subcutaneous implant, or orally in the form of capsules, powders, or granules. They may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

Active sesquiterpene lactone may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the active sesquiterpene lactone may be controlled by altering the concentration of the macromolecule.

Another method for controlling the duration of action comprises incorporating the active sesquiterpene lactone into particles of a polymeric substance such as a polyester, peptide, hydrogel, polylactide/glycolide copolymer, or ethylenevinylacetate copolymers. Alternatively, an active sesquiterpene lactone may be encapsulated in microcapsules prepared, for example, by coacervation techniques or by interfacial polymerization, for example, by the use of hydroxymethylcellulose or gelatin-microcapsules or poly (methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

A severe inflammatory disorder treated by the method of the present invention may be associated with expression of COX-2 or proinflammatory agents such as cytokines, TNF, IL-1, and MAPKS production, for example.

The present invention provides a method of treating or ameliorating a severe inflammatory disorder such as sepsis, endotoxemia, or septic shock, or one or more of the symptoms of sepsis; comprising administering to a subject displaying such symptoms or at risk for developing sepsis, a therapeutically effective amount of an active sesquiterpene lactone. The term "ameliorate" refers to a decrease or lessening of the symptoms of the disorder being treated. The symptoms that may be ameliorated include those associated with a transient increase in the blood level of TNF, such as fever, hypotension, neutropenia, leukopenia, thrombocytopenia, disseminated intravascular coagulation, adult respiratory distress syndrome, shock, and multiple organ failure. Patients who may benefit from such treatment include those at risk for or those suffering from toxemia, such as endotoxemia resulting from a Gram-negative bacterial infection, venom poisoning, or hepatic failure, for example. In addition, patients having a Gram-positive bacterial, viral, or fungal infection may also display symptoms of sepsis, and may also benefit from the therapeutic method described here.

Patients likely to benefit from the method of the present invention include those suffering from infection by Gram negative bacteria such as *E. coli, Haemophilus influenza B, Neisseria meningitides,* staphylococci, or pneumococci. Patients at risk for developing sepsis include those suffering from burns, gunshot wounds, renal failure, hepatic failure, trauma, burns, immunodepression (including HIV infection), hematopoietic neoplasias, multiple myeloma, Castleman's disease, or cardiac myxoma.

The term "therapeutically effective amount" as used herein for treatment of septicemia or endotoxemia refers to an amount of an active sesquiterpene lactone sufficient to decrease the subject's response to LPS, or to decrease the symptoms of sepsis or other severe inflammatory disorder. The term "therapeutically effective amount" therefore includes, for example, an amount of an active sesquiterpene lactone sufficient to prevent, and preferably to reduce by at least 50%, and more preferably sufficient to reduce by at least 90%, a clinically significant increase in a patient's plasma level of TNFα. The dosage ranges for the administration of active sesquiterpene lactone are those that produce the desired effect. Generally, the dosage will vary with the age, condition, and sex of the patient, and the extent of the infection. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the level of LPS, IL-1, and TNF in a patient. A decrease in serum LPS and TNF levels should correlate with recovery of the patient.

In addition, patients at risk for or exhibiting the symptoms of sepsis can be treated by the novel method, substantially simultaneous with the therapeutic administration of another TNF inhibitor. For example, administering an anti-TNF antibody or a TNF antagonist can help prevent or ameliorate the symptoms of sepsis. Particularly preferred is the use of an anti-TNF antibody as an active ingredient, such as a monoclonal antibody with TNF specificity as described by Tracey, et al. *Nature,* vol. 330, p. 662 (1987).

A patient who exhibits the symptoms of sepsis may also be treated with an antibiotic in addition to the treatment with active sesquiterpene lactone. Typical antibiotics include an amino-glycoside, such as gentamycin or a beta-lactam such as penicillin or cephalosporin. Therefore, a preferred therapeutic method includes administering a therapeutically effective amount of an active sesquiterpene lactone substantially simultaneously with administration of a bactericidal amount of an antibiotic. Preferably, administration of active sesquiterpene lactone occurs within about 48 hours and preferably within about 2–8 hours, and most preferably, substantially concurrently with administration of the antibiotic.

The term "bactericidal amount" refers to an amount sufficient to achieve a bacteria-killing blood concentration in the patient receiving the treatment. The bactericidal amounts of antibiotics generally recognized as safe for administration to a human are well known in the art, and as is known in the art, vary with the specific antibiotic and the type of bacterial infection being treated.

Administration of an active sesquiterpene lactone may also be used for ameliorating post-reperfusion injury. When treating arterial thrombosis, induction of reperfusion by clot lysing agents such as tissue plasminogen activator (t-PA) is often associated with tissue damage. Such tissue damage is thought to be mediated at least in part by leukocytes, including polymorphonuclear leukocytes (PMN). Administration of an active sesquiterpene lactone blocks leukocyte or PMN-endothelial interactions, and thereby diminish or prevent post-reperfusion injury.

The method is also useful in treating non-malignant or immunologically-related cell proliferative diseases such as psoriasis, pemphigus vulgaris, Behcet's syndrome, acute respiratory distress syndrome (ARDS), ischemic heart disease, post-dialysis syndrome, leukemia, acquired immune deficiency syndrome, septic shock, other types of acute inflammation, and lipid histiocytosis. Any disorder that is etiologically linked to the proinflammatory process (e.g., induction of IL-1, TNF-α, COX-2 expression) may be treated by this method.

While not wishing to be bound by a particular theory, it is believed that an active sesquiterpene lactone suppresses tyrosine phosphorylation of protein-tyrosine kinases, and that inhibition of COX-2 expression by an active sesquiterpene lactone is mediated at least in part by the inhibition of protein-tyrosine kinases.

The effectiveness of treatment may be monitored by detection methods used in the art, including immunoassays, Northern and Western blot analysis, and RNase protection assays. Examples of immunoassays that may be used to detect and monitor levels of cytokines, chemokines, mitogens, or other proteins affected by an active sesquiterpene lactone in a sample include competitive and non-competitive immunoassays, in either a direct or indirect format, such as a radioimmunoassay (RIA) or a sandwich (immunometric) assay. An immunoassay of a protein may be run in forward mode, reverse mode, or simultaneous modes, including competition immunoassays, and immunohistochemical assays on physiological samples. Monitoring is preferably performed by a forward immunoassay. Those of skill in the art will know, or can readily discern, other immunoassay monitoring formats without undue experimentation.

Solid phase-bound antibody molecules can be bound by adsorption from an aqueous medium, although other modes of fixation, such as covalent coupling or other known means of fixation to a solid matrix may be used. Preferably, the first antibody molecule is bound to a support before forming an immunocomplex with antigen (e.g., cytokine); however, the immunocomplex may also be formed prior to binding the complex to the solid support.

Non-specific protein binding sites on the surface of the solid phase support are preferably blocked. After adsorption of solid phase-bound antibodies, an aqueous solution of a protein free from interference with the assay—such as bovine, horse, or other serum albumin—that is also free from contamination with the antigen, is admixed with the solid phase to adsorb the admixed protein onto the surface of the antibody-containing solid support at protein binding sites on the surface that are not occupied by the antibody molecule.

A typical aqueous protein solution contains about 2–10 weight percent bovine serum albumin in phosphate-buffered saline (PBS) at a pH about 7–8. The aqueous protein solution-solid support mixture is typically maintained for a time period of at least one hour at a temperature of about 37–40° C., and the resulting solid phase is thereafter rinsed free of unbound protein.

The first antibody can be bound to different carriers and used to detect a cytokine or other protein in a sample. Examples of such carriers include glass, polystyrene, polypropylene, polyethylene, dextran, nylon, amyloses, natural and modified celluloses, polyacrylamides, agaroses, and magnetite. The carrier may be soluble or insoluble. Those skilled in the art will know of other suitable carriers for binding antibodies or antigen, or will be able to ascertain such carriers through routine experimentation.

In addition, if desired, an antibody in these immunoassays can be detectably labeled in various ways. There are many different labels and methods of labeling known to those skilled in the art. Examples of the types of labels which can be used in the present invention include enzymes, radioisotopes, fluorescent compounds, colloidal metals, chemiluminescent compounds, and bioluminescent compounds. Those of skill in the art will known of other suitable labels for binding to monoclonal antibodies, or will be able to ascertain such labels through routine experimentation. Furthermore, binding such labels to the antibodies may be performed with routine methods known in the art.

One of skill in the art may monitor the effect of an active sesquiterpene lactone on a protein kinase by measuring changes in the level of kinase activity. Such a measurement may comprise incubating the components, which include the kinase or a polynucleotide encoding the kinase and its substrate (e.g., Src tyrosine kinase and $p53/56^{lyn}$), under conditions conducive to interaction of the components, and then measuring the effect the composition has on kinase activity. For example, an increase or decrease in kinase activity may be measured by adding a radioactive compound to the mixture of components, such as $^{32}$P-ATP, and observing incorporation of radioactivity into the substrate to assay the compound's effect on protein kinase activity. A polynucleotide encoding the kinase may be inserted into an expression vector, and the effect of a composition on transcription of the kinase or stability of the mRNA may be measured, for example, by Northern blot analysis or RNase protection assay (see for example, Current Protocols in Molecular Biology, Ausubel, et al., *Wiley Interscience*, 1994, incorporated herein by reference). The level of cytokine, chemokine, mitogen, or other protein inhibited by an active sesquiterpene lactone may also be monitored by these and other standard techniques known to those of skill in the art.

The following examples are intended to illustrate but not limit the invention. While they are typical of those that might be used, other procedures otherwise known to those skilled in the art may alternatively be used.

EXAMPLE 1: Materials and Methods

1. Preparation of Parthenolide and Other Sesquiterpene Lactones

Parthenolide (compound 1 in FIG. 1) was extracted from dried leaves of *Magnolia grandiflora* as described originally by El-Feraly et al., *J. Pharma. Sci.*, vol. 67, 347–350 (1978). Encelin (compound 2 in FIG. 1) was extracted from *Encelia farinosa* as described by Geissman et al., *J. Org. Chem.*, vol. 33, p. 656 (1978). Leucanthin B and Melampodin A (Compounds 3 and 5, respectively, in FIG. 1) were extracted from *Melampodium leucanthum* as described by Fischer et al., *Phytochemistry*, vol. 14, p. 2241 (1975). Enhydrin (Compound 4 in FIG. 1) was extracted from *Polymnia uvedalia* as described by N. Fischer, *Rev. Latinoamer. Quim.*, vol. 9, p. 41 (1978). Confertiflorin (Compound 6 in FIG. 1) was extracted from *Ambrosia confertiflora* as described by Fischer et al., *Tetrahedron*, vol. 23, p. 2529 (1967). Burrodin (Compound 7 in FIG. 1) was extracted from *Ambrosia dumosa* as described by Geissman et al., *Phytochemistry*, vol. 7, p. 1613 (1968). Psilostachyin A (Compound 8 in FIG. 1) was extracted from *Ambrosia artemisiifolia* as described by Herz et al., *Phytochemistry*, vol. 12, p. 1415 (1975). Costunolide (Compound 9 in FIG. 1) was extracted from *Saussurea lappa* (Costus root oil) as described by Rao et al., *Tetrahedron*, vol. 9, p. 275 (1960). Tenulin (Compound 10 in FIG. 1) was extracted from *Helenium amarum* as described by Herz et al., *J. Amer. Chem. Soc.*, vol. 84, p. 3857 (1962). Compound 11, 11,13-dihydroparthenolide (FIG. 1), was extracted from *Ambrosia artemisiifolia*. Compound 12, 1(10)epoxy-11,13-dihydroparthenolide (FIG. 1), is a synthetic derivative of Compound 11. Santonin (Compound 13 in FIG. 1) is commercially available from Aldrich. The structural identities of parthenolide and other sesquiterpene lactones were determined spectroscopically ($^1$H and $^{13}$C NMR, IR, MS) as described in Fischer et al. (1979).

2. Isolation of Macrophages

Rat (Sprague-Dawley) alveolar macrophages were collected by broncho-alveolar lavage as described by Lee et al., J. Biol. Chem., vol. 267, pp. 25934–25938 (1992). The murine macrophage cell line RAW 264.7 (ATCC no. TIB-71) was cultured in Dubecco's modified Eagle's medium (DMEM) containing 10% heat-inactivated fetal bovine serum (FBS, Intergen). For the cyclooxygenase activity assay, cells were seeded in 24 well plates, and after near-confluency, cells were treated with aspirin (250 μM) for 2.5h to inactivate endogenous cyclooxygenase. The time course for the COX activity indicated that the maximum increase was reached in 8h. COX activity was determined by measuring prostaglandin $E_2$ concentrations in cells incubated with arachidonic acid (30 μM) for 10 minutes as described in Lee et al. (1992).

3. Antiphosphotyrosine Immunoblotting

This detection technique was carried out essentially as described in Chanmugan et al. (1995) using 4G10 monoclonal antiphosphotyrosine antibody (UBI) and the ECL detection system (Amersham).

4. Western Blot Analyses for COX-2, Interleukin-1α (IL-1α), c-Jun N-terminal Kinase-1 (JNK-1) and Glyceraldehyde-3-phosphate Dehydrogenase (GAPDH) Proteins The protein levels of COX-2 and GAPDH were assessed by Western blot analysis using polyclonal antibodies as described in Lee et al. (1992). Polyclonal antibodies for IL-1α and JNK-1 were purchased from Genzyme and Santa Cruz Biotech, respectively.

5. RNase Protection Assay

Total cellular RNA was isolated by TRIzoL reagent (Gibco, BRL). The RNase protection assay was performed as described in Chanmugan et al. (1995).

6. In-gel Kinase Assay

This assay was performed according to the method described by Kameshita et al., Anal. Biochem., vol. 183, pp. 139–143 (1989) using myelin basic protein (MBP) as a substrate.

EXAMPLE 2: Inhibition of the Expression of Cyclooxygenase and Proinflammatory Cytokines by Parthenolide in LPS-Stimulated Alveolar Macrophages Recovered COX activity in cells pretreated with aspirin reflected de novo synthesized COX-2. Alveolar macrophages pretreated with aspirin were incubated with LPS (10 μg/ml) and various concentrations of parthenolide for 16h. The activity of de novo synthesized COX-2 was determined by measuring the levels of $PGE_2$ produced from exogenous arachidonic acid. Activity of TNFα was determined by bioassay using L929 cells as described by Aggarwal et al., J. Biol. Chem., vol. 260, pp. 2345–2354 (1985). The dose-response to parthenolide in inhibiting the expression of COX activity showed that the $IC_{50}$ was about 0.8 μM as shown in FIG. 2. Values in FIG. 2 are the means of triplicate samples for TNFα and duplicate samples for $PGE_2$.

Similar inhibitions of the expression of COX-2 protein and steady state levels of COX-2 mRNA are shown in FIG. 3. In FIG. 3A, alveolar macrophages were incubated with LPS and various concentrations of parthenolide for 16h. Solubilized proteins were analyzed by COX-2, IL-1α or GAPDH immunoblotting. FIG. 3A is a representative immunoblot of more than five different analyses. Data are shown for various concentrations of both parthenolide (PTN) and herbimycin A (HER). Whether the suppression of the steady state levels of COX-2 mRNA by parthenolide was due to inhibition of the transcription rate or to accelerated degradation of mRNA is not known.

Figure 4A:
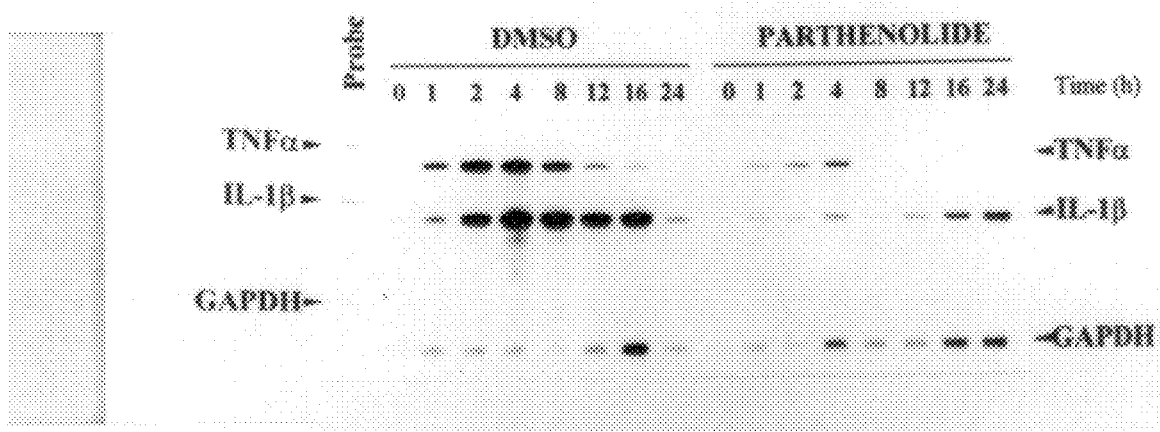
FIGS. 4A and 4B illustrate the time course for steady state levels of mRNA for TNFα, IL-1β, PTPase and GAPDH.
Figure 4B:
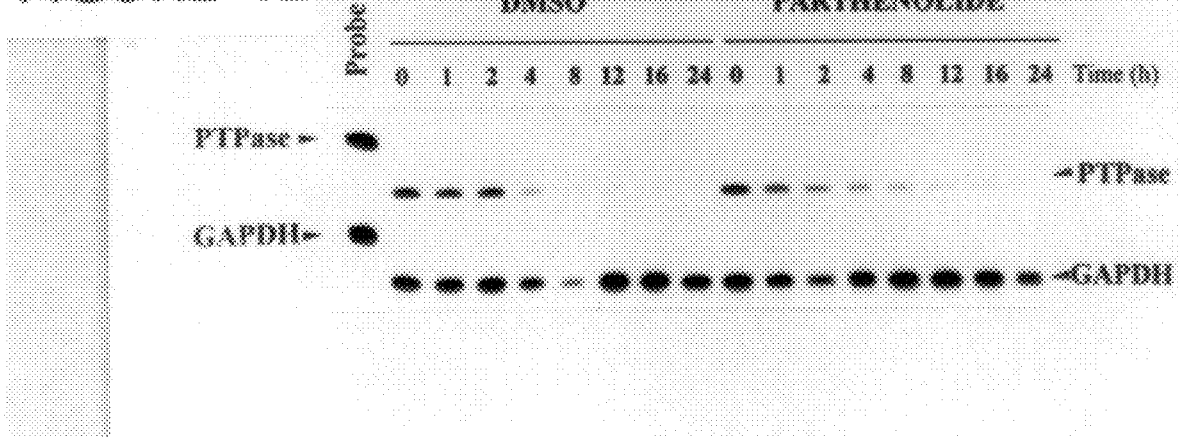

Parthenolide suppressed LPS-induced TNFα production with an $IC_{50}$ of 0.1 μg/ml, as seen in FIG. 2. Steady state levels of mRNA for TNFα and IL-1β were also inhibited by parthenolide as shown in FIG. 3B and FIG. 4. In FIG. 3B, alveolar macrophages were incubated with LPS in the presence of various concentrations of parthenolide for 2h. Steady state levels of mRNA were determined by RNase protection assay. In FIG. 4, alveolar macrophages were incubated with LPS in presence of 1 μg/ml of parthenolide for specified time periods. The concentrations of mRNA were determined by RNase protection assay.

Parthenolide inhibited the expression of IL-1α protein (non-secreted precursor form of IL-1) as determined by Western blot analysis as seen in FIG. 3A.

EXAMPLE 3. Parthenolide Suppresses Tyrosine Phosphorylation of Proteins, Including the Mitogen-Activated Protein Kinases (MAPKs)

The stimulation of macrophages by LPS results in the activation of MAPKs that lie at a central point in the multiple signal transduction pathways for various growth factors, hormones, and cytokines. Extracellular signal-regulated protein kinase 1 and 2 (ERK1 and ERK2) require phosphorylation of both Thr-183 and Tyr-185 for activation.

Parthenolide suppressed LPS-stimulated tyrosine phosphorylation of various proteins in RAW 264.7 cells as assessed by antiphosphotyrosine immunoblot, depicted in FIG. 5A. This inhibition was correlated with the suppressed expression of COX-2 and IL-1α. RAW 264.7 cells were pretreated with parthenolide in various concentrations or with herbimycin A (0.5 μg/ml) for 3h, and then stimulated with LPS (1 μg/ml) in the presence of the inhibitors for 30 min. FIG. 5 shows the dose-dependent inhibition of protein tyrosine phosphorylation and kinase activity of ERK-1 and ERK-2 by parthenolide and herbimycin A. FIG. 5A shows activity as measured by an antiphosphotyrosine immunoblot. The figure shows a representative immunoblot from more than five different analyses. Among these proteins, MAPKs exhibited the most dramatic inhibition in the extent of tyrosine phosphorylation in response to parthenolide. Parthenolide inhibition of tyrosine phosphorylation was most strongly inhibited in MAPKs. The tyrosine phosphorylation of three MAPK subfamily enzymes (ERK-1, ERK-2 and P38), which are all stimulated by LPS, was inhibited by parthenolide in a dose-dependent manner (FIG. 5A). The monoclonal antiphosphotyrosine antibody (4G10) did not recognize phosphorylated c-Jun N-terminal kinase-1 (JNK-1). Therefore, the extent of tyrosine phosphorylation of JNK-1 was assessed by the electrophoretic mobility shift of phosphorylated JNK-1 as shown in FIG. 5B. Parthenolide inhibited tyrosine phosphorylation of JNK-1. Another protein tyrosine kinase inhibitor, herbimycin A (a natural flavanoid), inhibited tyrosine phosphorylation of the MAPK subfamily.

The inhibition of tyrosine phosphorylation of MAPKs correlated with the inhibition of COX-2 and IL-1α expression in RAW 264.7 cells as shown in FIG. 5D.

Figure 6A:
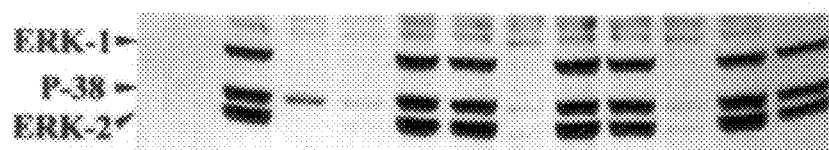
FIGS. 6A and 6B illustrate the suppression of the inhibitory effects of parthenolide on tyrosine phosphorylation of MAPKs and expression of COX-2 and IL-1α by certain sulfhydryl compounds.
Figure 6B:
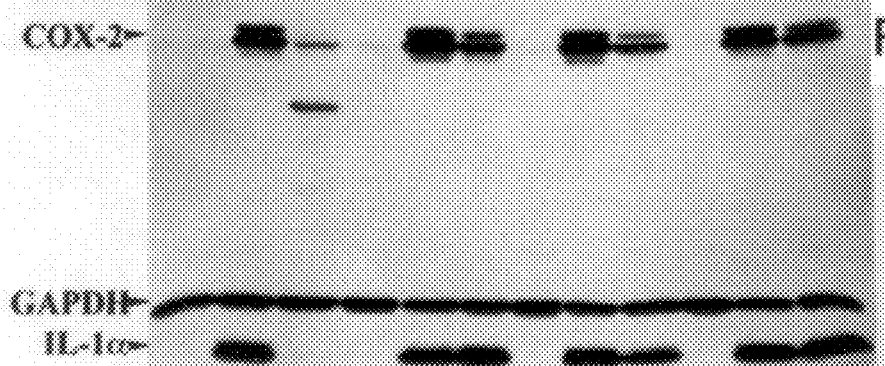

The mechanism by which parthenolide inhibits protein tyrosine phosphorylation is not currently known. It has been speculated that the tyrosine kinase inhibitor herbimycin A inactivates $p60^{v-src}$ kinase by irreversibly binding to the sulphydryl (SH) groups of p60$^{v-src}$ kinase. Y. Uehara et al., *Biochem. Biophys. Res. Commun.*, vol. 163, pp. 803–809 (1989). The inactivation by herbimycin may occur through conjugation between highly polarized double bonds in the benzoquinone moiety of herbimycin A and the SH group of sulphydryl compounds. Without wishing to be bound by this theory, the α-methylenebutyrolactone in parthenolide may interact with biological nucleophiles such as sulphydryl groups. Indeed, pretreating cells with sulphydryl compounds abrogated the inhibitory effect of parthenolide on LPS-induced activation of MAPKs as shown in FIG. 6A. In FIG. 6, RAW 264.7 cells were pretreated with parthenolide (1 μg/ml) in the presence of DTT (dithiothreitol, 100 μM), 2-ME (2-mercaptoethanol, 50 μM), or Cys (L-cysteine, 150 μM), and were then stimulated with LPS (1 μg/ml). Cells were incubated for 30 min for antiphosphotyrosine immunoblot analysis (FIG. 6A) and 8h for COX-2 and IL-1α Western blot analyses (FIG. 6B). Abolishing the inhibitory effect of parthenolide on the activation of MAPKs by these agents resulted in recovered expression of COX-2 and IL-1α that had been inhibited by parthenolide (FIG. 6B). These results imply that the inhibitory effects of parthenolide are mediated through conjugation with SH-groups of target proteins. However, these data alone do not permit an identification of the specific target protein(s) affected by parthenolide. Whether parthenolide inhibits protein tyrosine phosphorylation by directly inhibiting PTKs or by inhibiting other target protein(s) that affect the activity of PTKs is not currently known.

EXAMPLE 4. Structure—Function Relationships Among Sesquiterpene Lactones in Inhibiting COX-2 Expression Among the sesquiterpene lactones tested to date, parthenolide, encelin, and leucanthin B (Compounds 1, 2, and 3, respectively in Table 1 and FIG. 1) have shown the highest inhibitory activity.

TABLE 1

Relative potencies of different sesquiterpene lactones in inhibiting the expression of COX-2 in LPS-stimulated macrophages[a]

| Compound No. in FIG. 1 | Common Name | Mol. Wt. | IC$_{50}$ (μ/ml) |
|---|---|---|---|
| 1 | Parthenolide | 248 | 0.2 |
| 2 | Encelin | 244 | 0.1 |
| 3 | Leucanthin B | 478 | 0.2 |
| 4 | Enhydrin | 464 | 0.3 |
| 5 | Melampodin A | 444 | 0.5 |
| 6 | Confertiflorin | 306 | 0.9 |
| 7 | Burrodin | 264 | 1.0 |
| 8 | Psilostachyin A | 280 | 1.3 |
| 9 | Costunolide | 232 | 1.6 |
| 10 | Tenulin | 306 | 5.5 |
| 11 | 11,13-Dihydroparthenolide | 250 | >100 |
| 12 | 1(10)Epoxy-11,13-Dihydroparthenolide | 266 | >100 |
| 13 | Santonin | 246 | >100 |

[a]IC$_{50}$ was determined at multiple dose levels.

A common feature of the compounds with strong inhibitory activity was that they each possess an α-methylene-γ-lactone functional group, as well as another conjugation site. Compound 1, parthenolide, contains an epoxide moiety. Compound 2, encelin, in addition to the α-methylene-γ-lactone moiety possesses a cyclohexadienone structure, thus giving it three possible conjugation sites. Encelin was the most active compound tested. Compounds 3, 4 and 5 are examples of sesquiterpene lactones bearing epoxides(s) with α,β-unsaturated ester and α,β-epoxy ester side chains; these compounds exhibited activities similar to that of parthenolide.

Compounds 6 through 9 contain only the α-methylene-γ-lactone moiety, and their inhibitory activity was lower than that of compounds 1–5. Compound 10 is an example of a cyclopentenone; its activity was significantly less than that of compounds 1–9. Compounds 11 and 12, containing an epoxide moiety but no α-methylene-γ-lactone group, showed loss of inhibitory activity. Although the presence of an epoxide functionality appeared to accentuate the inhibitory activity of sesquiterpene lactones containing an α-methylene-γ-lactone group, an epoxide alone did not confer inhibitory activity to a sesquiterpene.

While not limiting the scope of the invention, examples of other active sesquiterpene lactones that may prove especially effective include ambrosin, aromaticin, burrodin, cinerenin, costunolide, chammissonin, coronopilin, confertiflorin, encelin, enhydrin, elephantopin, elephantin, eupatrindin, eupachlorin, euparotin, eupacunin, elephantol, eupahyssopin, eupatolide, eupaformosanin, farinosin, vernolepin, vernomenin, xanthanin, gaillardin, helenalin, leucanthin, ludovicin, liatrin, melampodin A and B, molephantin, molephantinin, mexicanin, parthenolide, paucin, parthenin, psilostachyin, tenulin, and tamaulipin.

EXAMPLE 5: Inhibition of Nuclear Factor—kB

Parthenolide inhibits Nuclear Factor—kB (NF-kB) transcription factor that has been activated by LPS in the murine macrophage cell line (RAW 264.7) as assessed by the degradation of the protein, IKB$_\alpha$. Activated NF-kB is known to induce the expression of many early response genes including inducible nitric oxide synthetase, cyclooxygenase, and chemokines that are implicated in acute inflammatory responses. Without wishing to be bound by this theory, this response may provide a part of the mechanism by which parthenolide inhibits the expression of COX-2, and further suggests that parthenolide also suppresses the production of nitric oxide and other proinflammatory cytokines.

EXAMPLE 6: In Vivo Experiments in Mice

Varying doses of parthenolide will be injected intraperitoneally into mice along with a lethal dose of LPS (1.5 mg/mouse). The mortality of the mice will be monitored for one week. Blood levels of TNFα will be monitored as described by Novogrodsky et al. (1994).

Once satisfactory data from laboratory animals have been obtained, clinical trials in human patients will be conducted in accordance with applicable statutes and regulations.

The complete disclosures of all references cited in this specification are hereby incorporated by reference. In the event of an otherwise irreconcilable conflict, however, the present specification shall control. Also incorporated by reference is the complete disclosure of the following paper, which is not prior art to the present invention: D. Hwang et al., "Inhibition of the Expression of Inducible Cyclooxygenase and Proinflammatory Cytokines by Sesquiterpene Lactones in Macrophages Correlates with the Inhibition of MAP Kinases," *Biochem. and Biophys. Res. Comm.*, vol. 226, pp. 810–818 (1996).

We claim:

1. A method of ameliorating or preventing, in a mammal, the symptoms of a severe inflammatory disorder that is associated with the production of an agent selected from the group consisting of endotoxin, protein-tyrosine kinase, cyclooxygenase-2, tumor necrosis factor alpha, interleukin- 1, interleukin-6, macrophage chemotactic protein, inducible nitric oxide synthetase, mitogen-activated protein kinase, macrophage inflammatory protein, interferon-gamma, tissue factor, granulocyte-macrophage-colony stimulating factor, and phosphotyrosine phosphatase; said method comprising administering to the mammal a therapeutically effective amount of an active sesquiterpene lactone, or a pharmaceutically acceptable salt of an active sesquiterpene lactone; wherein said active sesquiterpene lactone contains an $\alpha$-methylene-$\gamma$-lactone functional group.

2. The method of claim 1, wherein the agent is selected from the group consisting of tumor necrosis factor alpha and interleukin-1.

3. The method of claim 1, wherein the agent is selected from the group consisting of cyclooxygenase-2 and mitogen-activated protein kinase.

4. The method of claim 1, wherein the severe inflammatory disorder is selected from the group consisting of sepsis and septic shock.

5. The method of claim 1, additionally comprising the step of administering to the mammal a bactericidal amount of an antibiotic.

6. The method of claim 1, wherein the active sesquiterpene lactone contains a functional group selected from the group consisting of an epoxide, a cyclopentenone, a cyclohexenone, a cyclohexadienone, an $\alpha,\beta$-unsaturated ester, and an $\alpha, \beta$-epoxy ester.

7. The method of claim 1, wherein the active sesquiterpene lactone contains a functional group selected from the group consisting of an epoxide, a cyclohexadienone, an $\alpha,\beta$-unsaturated ester, and an $\alpha,\beta$-epoxy ester.

8. The method of claim 1, wherein the active sesquiterpene lactone contains a cyclohexadienone functional group.

9. The method of claim 1, wherein the active sesquiterpene lactone is encelin.

10. The method of claim 1, wherein the active sesquiterpene lactone is parthenolide.

11. The method of claim 1, wherein the active sesquiterpene lactone is leucanthin B.

12. The method of claim 1, wherein the active sesquiterpene lactone is enhydrin.

13. The method of claim 1, wherein the active sesquiterpene lactone is melampodin A.

14. The method of claim 1, wherein the active sesquiterpene lactone is tenulin.

15. The method of claim 1, wherein the active sesquiterpene lactone is confertiflorin.

16. The method of claim 1, wherein the active sesquiterpene lactone is burrodin.

17. The method of claim 1, wherein the active sesquiterpene lactone is psilostachyin A.

18. The method of claim 1, wherein the active sesquiterpene lactone is costunolide.

19. The method of claim 1, wherein the active sesquiterpene lactone is cinerenin.

20. The method of claim 1, wherein said administering of the active sesquiterpene lactone is performed by subcutaneous injection, intravenous injection, or transdermal absorption.

21. The method of claim 1, wherein the mammal is a human.

22. A method of ameliorating or preventing, in a mammal, the symptoms of a post-reperfusion injury that is associated with the production of an agent selected from the group consisting of endotoxin, protein-tyrosine kinase, cyclooxygenase-2, tumor necrosis factor alpha, interleukin-1, interleukin-6, macrophage chemotactic protein, inducible nitric oxide synthetase, mitogen-activated protein kinase, macrophage inflammatory protein, interferon-gamma, tissue factor, granulocyte-macrophage-colony stimulating factor, and phosphotyrosine phosphatase; said method comprising administering to the mammal a therapeutically effective amount of an active sesquiterpene lactone, or a pharmaceutically acceptable salt of an active sesquiterpene lactone; wherein said active sesquiterpene lactone contains an $\alpha$-methylene-$\gamma$-lactone functional group.

23. A method of ameliorating or preventing, in a mammal, the symptoms of a non-malignant or immunologically-related cell proliferative disease that is associated with the production of an agent selected from the group consisting of endotoxin, protein-tyrosine kinase, cyclooxygenase-2, tumor necrosis factor alpha, interleukin-1, interleukin-6, macrophage chemotactic protein, inducible nitric oxide synthetase, mitogen-activated protein kinase, macrophage inflammatory protein, interferon-gamma, tissue factor, granulocyte-macrophage-colony stimulating factor, and phosphotyrosine phosphatase; said method comprising administering to the mammal a therapeutically effective amount of an active sesquiterpene lactone, or a pharmaceutically acceptable salt of an active sesquiterpene lactone; wherein said active sesquiterpene lactone contains an $\alpha$-methylene-$\gamma$-lactone functional group.

24. The method of claim 23, wherein the disease is selected from the group consisting of psoriasis, pemphigus vulgaris, Behcet's syndrome, acute respiratory distress syndrome, ischemic heart disease, post-dialysis syndrome, acquired immune deficiency syndrome, and lipid histiocytosis.

* * * * *